United States Patent
Sebree et al.

(10) Patent No.: US 12,186,282 B2
(45) Date of Patent: **\*Jan. 7, 2025**

(54) TREATMENT OF 22Q11.2 DELETION SYNDROME WITH CANNABIDIOL

(71) Applicant: Harmony Biosciences Management, Inc., Plymouth Meeting, PA (US)

(72) Inventors: Terri Sebree, Gladwyne, PA (US); Donna Gutterman, Raleigh, NC (US)

(73) Assignee: HARMONY BIOSCIENCES MANAGEMENT, INC., Plymouth Meeting, PA (US)

( * ) Notice: Subject to any disclaimer, the term of this patent is extended or adjusted under 35 U.S.C. 154(b) by 82 days.

This patent is subject to a terminal disclaimer.

(21) Appl. No.: 17/957,932

(22) Filed: Sep. 30, 2022

(65) Prior Publication Data

US 2023/0024756 A1    Jan. 26, 2023

Related U.S. Application Data

(63) Continuation of application No. 16/712,066, filed on Dec. 12, 2019, now Pat. No. 11,458,109.

(60) Provisional application No. 62/895,279, filed on Sep. 3, 2019, provisional application No. 62/779,591, filed on Dec. 14, 2018.

(51) Int. Cl.
| A61K 31/05 | (2006.01) |
| A61K 9/00 | (2006.01) |
| A61K 9/06 | (2006.01) |
| A61P 25/22 | (2006.01) |

(52) U.S. Cl.
CPC ............ *A61K 31/05* (2013.01); *A61K 9/0014* (2013.01); *A61K 9/06* (2013.01); *A61P 25/22* (2018.01)

(58) Field of Classification Search
CPC ..................................................... A61K 31/05
See application file for complete search history.

(56) References Cited

U.S. PATENT DOCUMENTS

| | | | |
|---|---|---|---|
| 7,423,026 B2 | 9/2008 | Jarvinen et al. | |
| 8,293,786 B2 | 10/2012 | Stinchcomb et al. | |
| 8,435,556 B2 | 5/2013 | Stinchcomb et al. | |
| 8,449,908 B2 | 5/2013 | Stinchcomb et al. | |
| 9,375,417 B2 | 6/2016 | Smith et al. | |
| 9,447,019 B2 | 9/2016 | Mechoulam et al. | |
| 9,533,942 B2 | 1/2017 | Stinchcomb et al. | |
| 9,675,656 B2 | 6/2017 | Crowley | |
| 9,730,911 B2 | 8/2017 | Verzura et al. | |
| 9,782,360 B2 | 10/2017 | Mechoulam et al. | |
| 9,943,491 B2 | 4/2018 | De Vries et al. | |
| 10,213,390 B1 | 2/2019 | Bonn-Miller et al. | |
| 10,314,792 B2 | 6/2019 | Sebree et al. | |
| 10,471,022 B2 | 11/2019 | Bonn-Miller et al. | |
| 10,555,928 B2 | 2/2020 | Blackmon et al. | |
| 10,568,848 B2 | 2/2020 | Sebree et al. | |
| 10,716,766 B2 | 7/2020 | Aung-Din | |
| 10,758,497 B2 | 9/2020 | Bonn-Miller et al. | |
| 11,458,109 B2 * | 10/2022 | Sebree ................. | A61K 31/035 |
| 2008/0139472 A1 | 6/2008 | Lauterborn et al. | |
| 2010/0273895 A1 | 10/2010 | Stinchcomb et al. | |
| 2011/0052694 A1 | 3/2011 | Stinchcomb et al. | |
| 2015/0342902 A1 | 12/2015 | Vangara et al. | |
| 2015/0343071 A1 | 12/2015 | Vangara et al. | |
| 2016/0000843 A1 | 1/2016 | Lowe et al. | |
| 2016/0022627 A2 | 1/2016 | Smith | |
| 2016/0256410 A1 | 9/2016 | Aung-Din | |
| 2016/0256411 A1 | 9/2016 | Aung-Din | |
| 2016/0271252 A1 | 9/2016 | Vangara et al. | |
| 2016/0338974 A1 | 11/2016 | Aung-Din | |
| 2017/0224634 A1 | 8/2017 | Vangara et al. | |
| 2017/0231923 A1 | 8/2017 | Guy et al. | |
| 2017/0274030 A1 | 9/2017 | Crowley | |
| 2017/0348276 A1 | 12/2017 | Bryson et al. | |
| 2017/0360745 A1 | 12/2017 | Blackmon et al. | |
| 2018/0140560 A1 | 5/2018 | De Vries et al. | |
| 2019/0117619 A1 | 4/2019 | Guy et al. | |
| 2020/0188324 A1 | 6/2020 | Sebree et al. | |
| 2020/0360299 A1 | 11/2020 | Bonn-Miller et al. | |
| 2021/0196669 A1 | 7/2021 | Bar-Lev Schleider et al. | |
| 2021/0369643 A1 | 12/2021 | Sebree et al. | |
| 2021/0401769 A1 | 12/2021 | Griesser et al. | |
| 2022/0096396 A1 | 3/2022 | Sebree et al. | |
| 2023/0024756 A1 | 1/2023 | Sebree et al. | |
| 2023/0059709 A1 | 2/2023 | Palumbo et al. | |
| 2023/0364028 A1 | 11/2023 | Sebree et al. | |
| 2023/0414533 A1 | 12/2023 | Bonn-Miller et al. | |
| 2024/0122873 A1 | 4/2024 | Griesser et al. | |

FOREIGN PATENT DOCUMENTS

| AU | 2018101357 A4 | 10/2018 |
| CN | 107126411 A | 9/2017 |

(Continued)

OTHER PUBLICATIONS

U.S. Appl. No. 16/737,326.
U.S. Appl. No. 17/895,008.
U.S. Appl. No. 17/941,739.
U.S. Appl. No. 17/942,068.
Busquets-Garcia, Arnau, et al., Targeting the endocannabinoid system in the treatment of fragile X syndrome, Nature Medicine (Mar. 2013).

(Continued)

*Primary Examiner* — Paul V Ward

(74) *Attorney, Agent, or Firm* — WOMBLE BOND DICKINSON (US) LLP; Danielle L. Herritt; Mark R. DeLuca

(57) ABSTRACT

The present technology relates to methods of treating one or more behavioral symptoms (for example, anxiety) of 22q 11.2 deletion syndrome in a subject by administering, e.g., transdermally, an effective amount of cannabidiol (CBD) to the subject wherein one or more behavioral symptoms of 22q 11.2 deletion syndrome are treated in the subject.

20 Claims, 1 Drawing Sheet

(56) References Cited

FOREIGN PATENT DOCUMENTS

| | | |
|---|---|---|
| GB | 2549278 A | 10/2017 |
| WO | 2006133941 A2 | 12/2006 |
| WO | WO-2010127033 A1 | 11/2010 |
| WO | WO-2016109624 A1 | 7/2016 |
| WO | 2016141056 A1 | 9/2016 |
| WO | WO-2017068349 A1 | 4/2017 |
| WO | WO-2017149387 A1 | 9/2017 |
| WO | WO-2017151980 A1 | 9/2017 |
| WO | WO-2017158539 A1 | 9/2017 |
| WO | WO-2017178807 A1 | 10/2017 |
| WO | WO-2017178810 A1 | 10/2017 |
| WO | WO-2017182950 A1 | 10/2017 |
| WO | 2018011808 A1 | 1/2018 |
| WO | WO-2018002637 A1 | 1/2018 |
| WO | WO-2018109471 A1 | 6/2018 |
| WO | 2019034985 A1 | 2/2019 |
| WO | 2019089583 A1 | 5/2019 |
| WO | 2022017942 A1 | 1/2022 |

OTHER PUBLICATIONS

International Search Report and Written Opinion of corresponding PCT/IB2019/060735, mailed Mar. 3, 2020, 12 pages.
Banks S, O'Neill C, Sebree T. Pharmacokinetic Evaluation of Subcutaneously Administered ZYN001 in Male Sprague-Dawley Rats. PAINWeek. Sep. 8-12, 2015.
Bergmaschi et al., Cannabidiol Reduces the Anxiety Induced by Simulated Public Speaking in Treatment-Naiver Social Phobia Patients, Neuropsychopharmacology (2011) 36, 1219-1226.
Blessing et al., Cannibidiol as a Potential Treatment for Anxiety Disorders, Neurotherapeutics, Oct. 2015, 12(4): 825-836.
Bonn-Miller M, Banks SL, Sebree T. Conversion of Cannabidiol Following Oral Administration: Authors' Response to Grotenhermen et al. Cannabis and Cannabinoid Research 2017;2:1, 5-7.
Bonn-Miller M, Gutterman D. A Permeation-Enhanced Synthetic Cannabidiol (CBD) Transdermal Gel for the Treatment of PTSD. Military Health System Research Symposium. Orlando, FL. Aug. 15-18, 2016.
Bonn-Miller M, Sebree T, O'Neill C, Messenheimer J. Neuropsychological Effects of ZYN002 (Synthetic Cannabidiol) Transdermal Gel in Healthy Subjects and Patients with Epilepsy: Phase 1, Randomized, Double-Blind, Placebo-Controlled Studies. American Epilepsy Society Annual Meeting. Houston, TX. Dec. 2-6, 2016.
Fusar-Poli, et al., "Modulation of Effective Connectivity During Emotional Processing by A9- tetrahydrocannabinol and Cannabidiol," International Journal of Neuropsychopharmacology (2010) 13, 421-432.
Gauvin D, O'Neill C, Patterson DR. Respiratory Evaluation of Subcutaneously Administered ZYN001 in Male Sprague-Dawley Rats. PAINWeek. Sep. 8-12, 2015.
Jung KM, Sepers M, et al. Uncoupling of the endocannabinoid signalling complex in a mouse model of fragile X syndrome. Nat Commun 2012;3:1080.
Kidd, et al., Cannabinoids in the Treatment of Autism Spectrum Disorder: Demanding Data Before Using Fad Therapies, Pediatric Neurology, 88 (2018) 10-11.
Lozano, et al., "Advances in the Understanding of Gabaeric Neurobiology of FMR1 Expanded Alleles Leading to Targeted Treatments for Fragile X Spectrum Disorder," Curr Pharm Des Author manuscript, (2015); 21 (34): 4972-4979.
Merrick J, Lane B, Sebree T, Yaksh T, O'Neill C, Banks SL. Identification of psychoactive degradants of cannabidiol in simulated gastric and physiological fluid. *Cannabis and Cannabinoid Research* 2016;1:1, 102-112, DOI: 10.1089/can.2015.0004.
Novagant Corp. Announces Breakthrough in Cannabidiol (CBD) Transdermal Patch for Localized Delivery, Oct. 29, 2014.
O'Brien T MD, FRACP; Berkovic, S, MD, FRACP; French, J, MD, et al. Synthetic Transdermal Cannabidiol for the Treatment of Focal Epilepsy in Adults. 2017 American Epilepsy Society Annual Meeting, Washington, DC. Dec. 1-5, 2017.
Paudel KS, Hammell DC, et al. Cannabidiol bioavailability after nasal and transdermal application: effect of permeation enhancers. Drug Development and Industrial Pharmacy 2010;36(9):1088-1097.
Qin M, Zeidler Z, et al. Endocannabinoid-mediated improvement on a test of aversive memory in a mouse model of fragile X syndrome. Behav Brain Res Sep. 15, 2015;291:164-71.
Salgado, et al., Autism Spectrum Disorder and Cannabidiol: Have We Seen This Movie Before?, Global Pediatric Health, vol. 5:1-5 (2018).
Sativex Product Monograph, Buccal Spray, Mar. 30, 2012 (55 pages).
Sebree T, O'Neill C, Messenheimer J, Gutterman D. Safety and Tolerability of ZYN002 (Synthetic Cannabidiol) Transdermal Permeation-Enhanced Gel in Healthy Subjects and Epilepsy Patients: Three Phase 1, Randomized, Double-Blind, Placebo-Controlled Studies. American Epilepsy Society Annual Meeting. Houston, TX. Dec. 2-6, 2016.
Wei, et al., Enhancement of Anandamide-Mediated Endocannabinoid Signally Corrects Autism-Related Social Impairment, Cannabis and Cannabinoid Research, vol. 1.1 (2016).
Wheeler, et al., "Anxiety, Attention Problems, Hyperactivity, and the Aberrant Behavior Checklist in Fragile X Syndrome," American Journal of Medical Genetics, (2013) 141-155.
Winton-Brown, et al., "Modulation of Auditory and Visual Processing by Delta-9-Tetrahydrocannabinol and Cannabidiol: an fMRI Study," Neuropsychopharmacology (2011) 36, 1340-1348.
Hadland, S., et al., "Medical Marijuana: Review of the Science and Implications for Developmental Behavioral Pediatric Practice," J Dev Behav Pediatr. 2015 ; 36(2): 115-123.
Aran, A., et al., "Cannabidiol Based Medical Cannabis in Children with Autism—a Retrospective Feasibility Study (P3.318)," Neurology, 90:15 Supplement, (2018).
Pavlovic, Zoran M., "Cannabinoids in Autism and Fragile X Syndrome: Value-Based Treatment Revolution Ahead?," Global Journal of Intellectual & Developmental Disabilities, 3(1) 1-4 (Sep. 2017).
Khalil, Rami Bou, "Would some cannabinoids ameliorate symptoms of autism?", European Child & Adolescent Psychiatry, 21(4):237-238, XP035037636, ISSN: 1435-165X, DOI: 10.1007/S00787-012-0255-Z (2017).
Anonymous: History of Changes for Study: NCT02956226, "Cannabinoids for Behavioral Problems in Children with ASD (CBA)", XP055718101, Retrieved from the Internet: URL:https://clinicaltrials.gov/ct2/history/NCT02956226?V_4=View#StudyPageTop [retrieved on Jul. 27, 2020] (2017).
Hammell, D.C., et al., "Transdermal cannabidiol reduces inflammation and pain-related behaviours in a rat model of arthritis", Eur. J. Pain, vol. 20(6):936-948. doi:10.1002/ejp.818 (Jul. 2016).
Heussler, Helen et al., "A phase 1/2, open-label assessment of the safety, tolerability, and efficacy of transdermal cannabidiol (ZYN002) for the treatment of pediatric fragile X syndrome", Journal of Neurodevelopmental Disorders, vol. 11, No. 1, pp. 1-9, XP055828347 (2019).
Belmonte, Matthew K., et al., "Fragile X syndrome and autism at hte intersection of genetic and neural networks", Nature Neuroscience, vol. 9(10):1221-1225 (2006).
Hagerman, Randi, et al., "Fragile X Syndrome and Targeted Treatment Trials", National Institutes of Health Public Access Manuscript, published as Results Probl Cell Differ., vol. 54:297-335. doi:10.1007/978-3-642-21649-7_17 (2012).
Kaufmann, Walter E., et al., "Autism Spectrum Disorder in Fragile X Syndrome: Cooccurring Conditions and Current Treatment", HHS Public Access Manuscript, published as Pediatrics, vol. 139(Suppl 3):S194-S206. doi:10.1542/peds.2016-1159F (2017).
Pisante, S., et al., "Cannabidiol: State of the Art and New Challenges for Therapeutic Applications", Pharmacology and Therapeutics, vol. 175, pp. 133-150 (2017).
Mechoulam, Raphael, et al., "Cannabidiol: An Overview of Some Pharmacological Aspects", The Journal of Clinical Pharmacology, vol. 42, Issue 51, pp. 11S-19S (2002).
Mechoulam, Raphael, et al., "Cannabidiol—Recent Advances", Chemistry & Biodiversity; vol. 4, pp. 1678-1692 (2007).

(56) References Cited

OTHER PUBLICATIONS

Zynerba Pharmaceuticals Announces Top-Line Results from Phase 2 STAR 1 Trial of ZYN002 in Adult Epilepsy Patients with Focal Seizures (Aug. 7, 2017).
Hagerman, Randi J., et al., "Fragile X-Associated Neuropsychiatric Disorders (FXAND)," Frontiers in Psychiatry, vol. 9. Article 564, pp. 1-9 (2018).
Crawford, Dana C., et al., "FMR1 and the Fragile X Syndrome: Human Genome Epidemiology Review," Genet. Med., Author manuscript, HHS Public Access, vol. 3(5):359-371 (2001).
Godler, David Eugeny, et al., "Methylation of novel markers of fragile X alleles is inversely correlated with FMRP expression and FMR1 activation ratio," Human Molecular Genetics, vol. 9(18):1618-1632 (2010).
SDCAadmin, "The Difference Between Moderate to Severe Autism," Sarah Dooley Center for Autism, pp. 1-6 (2019).
Aran, Adi, et al., "Brief Report: Cannabidiol-Rich Cannabis in Children with Autism Spectrum Disorder and Severe Behavioral Problems—A Retrospective Feasibility Study," Journal of Autism and Developmental Disorders, vol. 49:1284-1288 (2019).
Hagerman, Randi J., et al., "High Functioning Fragile X Males: Demonstration of an Unmethylated Fully Expanded FMR-1 Mutation Associated with Protein Expression," American Journal of Medical Genetics, vol. 51:298-308 (1994).
International Preliminary Report on Patentability for corresponding PCT/US2022/078449 dated Apr. 24, 2024, 9 pages.
Ali, Shayma et al., "Efficacy of cannabinoids in paediatric epilepsy", Developmental Medicine & Child Neurology, vol. 61:13-18 (2019).
Kuchenbuch, Mathieu, et al., "Add-on cannabidiol significantly decreases seizures in 3 patients with SYNGAP1 developmental and epileptic encephalopathy," Epilepsia Open, vol. 5:496-500 (2020).
SynGAP Research Fund, Webinar, CBD, Seizures & SynGAP: Parents Experience (2019).
Vlaskamp, Danique R.M., et al., "SYNGAP1 encephalopathy: A distinctive generalized developmental and epileptic encephalopathy," Neurology, vol. 92(2):e96-e107 (2019).
"Lacking guidance from doctors, parents lead the charge in treating children with CBD," Peninsula Press (2018).
Salcedo-Arellano, Maria Jimena, et al., "Overlapping Molecular Pathways Leading to Autism Spectrum Disorders, Fragile X Syndrome, and Targeted Treatments", Neurotherapeutics, Springer International Publishing, Cham, vol. 18, No. 1, pp. 265-283 (2020).

International Search Report and Written Opinion for corresponding PCT/US2022/078449 mailed Feb. 2, 2023, 13 pages.
Hagerman, Paul J., Ph.D., M.D et al., Fragile X Syndrome: Diagnosis, Treatment, and Research, The Johns Hopkins University Press, pp. 210, 213, 471 and 472, 3rd Edition (2002).
Liu, X. Shawn, et al., Rescue of Fragile X Syndrome Neurons by DNA Methylation Editing of the FRM1 Gene, Cell Press, vol. 172:979-992 (2018).
Payan Gomez, Cesar, et al., "Variable Expressivity in Fragile X Syndrome: Towards the Identification of Molecular Characteristics That Modify the Phenotype", The Application of Clinical Genetics, DovePress, vol. 14:305-312 (2021).
Clinical Leader: Zynerba Pharmaceuticals Achieves Target Enrollment in Exploratory Phase 2 Trial of ZYN002 in Fragile X Syndrome, retrieved from the internet at URL:<https://www.clinicalleader.com/doc/zynerba-pharmaceuticals-achieves-target-exploratoryphase-syndrome-0001>, retrieved on Aug. 31, 2023 (2017).
Buckner, Julia D., et al., "Cannabis-related impairment and social anxiety: the roles of gender and cannabis use motives", Addictive Behaviors, vol. 37(11):1294-1297 (2012).
Fung, Wai Lun Alan, et al., "Elevated Prevalence of Generalized Anxiety Disorder in Adults 22q11.2 Deletion Syndrome", American Journal of Psychiatry, vol. 167(8):998, XP009553437 (2010).
Siegel, Steven, et al., Transdermal Cannabidiol (CBD) Gel for the Treatment of Fragile X Syndrome (FXS), ACNP 57th Annual Meeting: Poster Session III, Neuropsychopharmacology, vol. 43, Suppl. 1, pp. S399-S400, XP093109132 (2018).
International Search Report and Written Opinion for corresponding PCT/IB2021/054543 dated Dec. 8, 2021, 10 pages.
International Preliminary Report on Patentability for corresponding PCT/IB2021/054543 dated Nov. 17, 2022, 7 pages.
Maneeton, Narong, et al., "Risperidone for children and adolescents with autism spectrum disorder: a systematic review", Neuropsychiatric Disease and Treatment, vol. 14:1811-1820 (2018).
National Library of Medicine; Natonal Center for Biotechnology Information; PubChem; Compound Summary—Cannabidiol; 67 pages (2014).
Heussler, H. et al., "Transdermal cannabidiol (CBD) Gel for the treatment of fragile X syndrome (FXS)", 57th Annual Meeting of the American College of Neuropsychopharmacology (ACNP), Hollywood, FL. 2018, Poster P5-092, <URL: https://www.zynerba.com/wp-content/uploads/2019/05/Transdermal-Cannabidiol-CBD-Gel-for-the-Treatment-of-Fragile-X-Syndrome.pdf>.

* cited by examiner

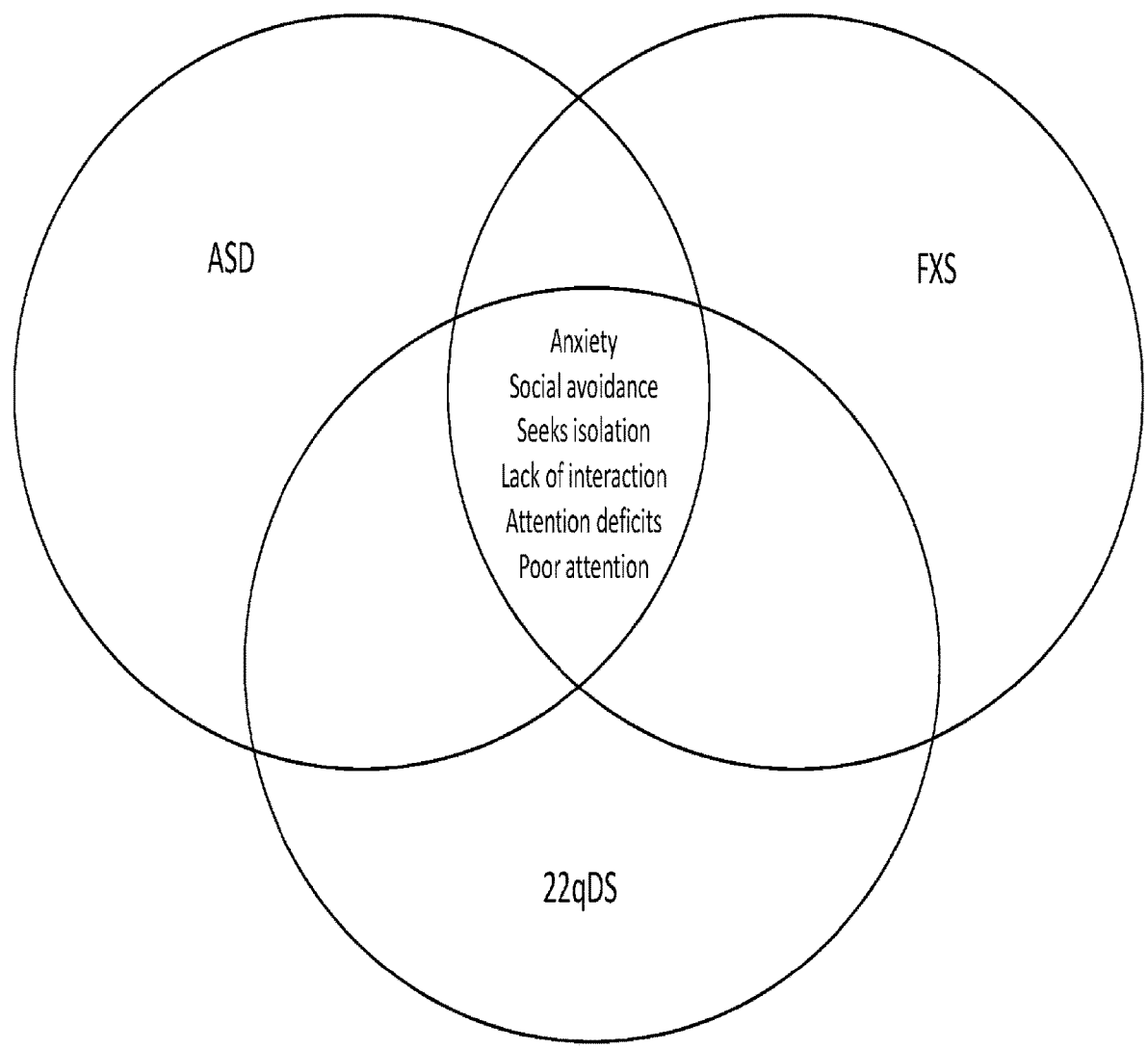

TREATMENT OF 22Q11.2 DELETION SYNDROME WITH CANNABIDIOL

CROSS REFERENCE TO RELATED APPLICATIONS

This application is a continuation application of U.S. patent application Ser. No. 16/712,066 filed Dec. 12, 2019, currently allowed, which claims the benefit of and priority to U.S. Provisional Application No. 62/779,591 filed Dec. 14, 2018 and U.S. Provisional Application No. 62/895,279 filed Sep. 3, 2019. The contents of each of which are hereby incorporated herein in their entirety.

FIELD OF THE TECHNOLOGY

The present disclosure relates to methods of treating one or more behavioral symptoms (for example, anxiety) of 22q11.2 deletion syndrome in a subject by administering an effective amount of cannabidiol (CBD) to the subject wherein one or more behavioral symptoms of 22q11.2 deletion syndrome are treated in the subject.

BACKGROUND

Cannabinoids are a class of chemical compounds found in the *Cannabis* plant. The two primary cannabinoids contained in *Cannabis* are cannabidiol, or CBD, and Δ9-tetrahydrocannabinol, or THC. CBD lacks the psychoactive effects of THC. Studies have shown that CBD can be used to treat disorders such as epilepsy, arthritis, and cancer.

22q11.2 deletion syndrome is caused by a hemizygous microdeletion of chromosome 22. The deletion of chromosome 22 occurs near the middle of the chromosome at a location designated as q11.2. The deletion results in the poor development of several body systems. The symptoms associated with 22q11.2 deletion syndrome vary in both the number of symptoms that are present in a human suffering from 22q11.2 deletion syndrome as well as the severity of each symptom. Prominent neuropsychiatric and phenotypic features include heart defects, poor immune system function (which can lead to recurrent infections), a cleft palate, complications related to low levels of calcium in the blood, and delayed development with both emotional and behavioral issues, cognitive impairment, anxiety, ADHD, and development of psychosis in late adolescent or early adulthood.

Children with 22q11.2 deletion syndrome can have developmental delays, which can include delayed speech, growth and learning disabilities. "Later in life, they are at an increased risk of developing mental illnesses such as schizophrenia, depression, anxiety, and bipolar disorder." (Genetics Home Reference, U.S. National Library of Medicine, 22q11.2 deletion syndrome, https://ghr.nlm.nih.gov/condition/22q112-deletion-syndrome.)

SUMMARY

The present disclosure relates to a method of treating one or more behavioral symptoms of 22q11.2 deletion syndrome in a subject. The method includes administering an effective amount of cannabidiol (CBD) to the subject wherein one or more behavioral symptoms of 22q11.2 deletion syndrome are treated in the subject. Administering the CBD includes transdermally or orally administering.

In some embodiments, the CBD is (−)-CBD. The effective amount of CBD can be between about 50 mg to about 1000 mg daily. In some embodiments, the effective amount of CBD is initiated at about 50 mg daily and titrated up to about 500 mg daily dose or about 1000 mg daily. The effective amount of CBD can be initiated at about 50 mg daily and titrated up to about 250 mg daily. In some embodiments, the effective amount of CBD is initiated at 250 mg daily. The effective amount of CBD can be initiated at 500 mg daily. In some embodiments, the 500 mg daily dose and the 1000 mg daily dose is administered to patients that weigh greater than 35 kg. The CBD can be administered in a single daily dose or in two daily doses. In some embodiments, the effective amount of CBD can be 390 mg in divided daily doses.

The CBD can be formulated as a gel or an oil. In some embodiments, the CBD is formulated as a permeation-enhanced gel. The gel can contain between 1% (wt/wt) CBD to 7.5% (wt/wt) CBD. In some embodiments, the gel contains 4.2% (wt/wt) CBD. In some embodiments, the gel contains 7.5% (wt/wt) CBD.

In some embodiments, the transdermal preparation can be a cream, a salve or an ointment. The CBD can be delivered by a bandage, pad or patch.

Alleviating one or more behavioral symptoms of 22q11.2 deletion syndrome can include treating or alleviating general anxiety. Anxiety is the symptom that caregivers of children with 22q11.2 deletion syndrome found the most burdensome and desired treatment to relieve the anxiety, which can improve overall quality of life.

Other symptoms that can be alleviated include psychosis, mood disorders, emotional and behavioral issues, and/or attention-deficit/hyperactivity disorder (ADHD).

The CBD can be administered transdermally on the subject's upper arm and shoulder. In some embodiments, the CBD is administered transdermally on the subject's thigh or back.

The CBD can be synthetic CBD. The CBD can be purified CBD. The CBD can be botanically derived.

In some embodiments, transdermally administering an effective amount of cannabidiol (CBD) can reduce an intensity of at least one adverse event or side effect relative to orally administering CBD. The at least one adverse event or side effect can be a gastrointestinal (GI) adverse event. The at least one adverse event or side effect can be liver function. In some embodiments, the at least one adverse event is somnolence. In some embodiments, the frequency and intensity of somnolence is reduced as an adverse event.

BRIEF DESCRIPTION OF THE DRAWINGS

FIG. 1 is a Venn diagram showing the common behavioral features of ASD, FXS, and 22qDS, according to an illustrative embodiment of the technology.

DETAILED DESCRIPTION

As used herein, the term "treating" or "treatment" refers to mitigating, improving, relieving, or alleviating at least one symptom (such as a behavioral symptom) of a condition, disease or disorder in a subject, such as a human, or the improvement of an ascertainable measurement associated with a condition, disease or disorder.

As used herein, the term "clinical efficacy" refers to the ability to produce a desired effect in humans as shown through a Food and Drug Administration (FDA), or any foreign counterparts, clinical trial.

As used herein, the term "cannabidiol" or "CBD" refers to cannabidiol; cannabidiol prodrugs; pharmaceutically acceptable derivatives of cannabidiol, including pharmaceutically acceptable salts of cannabidiol, cannabidiol prodrugs, and cannabidiol derivatives. CBD includes, 2-[3-methyl-6-(1-methylethenyl)-2-cyclohexen-1-yl]-5-pentyl-1,3-benzenediol as well as to pharmaceutically acceptable salts, solvates, metabolites (e.g., cutaneous metabolites), and metabolic precursors thereof. The synthesis of CBD is described, for example, in Petilka et al., *Helv. Chim. Acta,* 52:1102 (1969) and in Mechoulam et al., *J. Am. Chem. Soc.,* 87:3273 (1965), which are hereby incorporated by reference.

As used herein, the term "transdermally administering" refers to contacting the CBD with the patient's or subject's skin under conditions effective for the CBD to penetrate the skin.

The Drug Product ZYN002 is a transdermal cannabidiol (CBD) gel. CBD is the primary non-euphoric cannabinoid in the *Cannabis sativa* L plant. The CBD contained within ZYN002 is a pharmaceutically produced Active Pharmaceutical Ingredient (API) that is chemically identical to the CBD present in *Cannabis*.

*Cannabis* has low affinity for $CB_1$ and $CB_2$ receptors, and CBD produces multiple effects, including blocking the equilibrative nucleoside transporter, the orphan G-protein receptor GPR 55, and the transient receptor potential of ankyrin type 1 channel, and regulating the intracellular effects of calcium. The influence of CBD on these targets, each of which is known to play a role in neuronal excitability, is the scientific basis for its antiepileptic potential. The expectation of a wide margin of safety in humans was founded on the results of well-controlled studies in which CBD has exhibited high tolerability across several modes of administration.

ZYN002 is being developed as a clear, transdermal gel to provide consistent, controlled cannabidiol (CBD) delivery with twice daily (every 12 hours [Q12 H]) dosing. Because CBD is virtually insoluble in water, ethanol and propylene glycol are used as solubilizing agents and diethylene glycol monoethyl ether (brand name: Transcutol® HP) is used as a permeation enhancer.

22q11.2 deletion syndrome (also referred to as 22qDS) is caused by a hemizygous microdeletion of chromosome 22. The deletion of chromosome 22 occurs near the middle of the chromosome at a location designated as q11.2. The deletion results in the poor development of several body systems. The most common symptoms of 22q11.2 deletion syndrome are heart defects (74% of individuals), abnormalities with the development of the palate (69% of individuals), characteristic facial features (elongated face, almond-shaped eyes, wide nose, and small ears), learning difficulties (70-90% of individuals) including significant delay in the development of language (70% will have minimal words by 24 months of age), and immune system problems.

22q11.2 deletion syndrome is the most common (yet under-diagnosed) microdeletion syndrome affecting 1 in 2,000 to 1 in 4,000 live births. Approximately 50 genes are affected resulting in effects on multiple body systems. 22q11.1DS is inherited as autosomal dominant but 90-95% cases are spontaneous (McDonald-McGinn et al, "22q11.2 deletion syndrome" *Nat Rev Dis Primers;*1:15071.doi: 10.1038/nrdp.2015.71, 2015). Patients usually harbor a 1.5 to 3 Mb hemizygous deletion at chromosome 22q11.2, resulting in pathognomonic T-Box Protein 1(TBX1), adaptor protein CRKL and/or mitogen-activated protein kinase 1 (MAPK1) haplo-insufficiency.

The clinical presentations of 22qDS are highly variable within and between families, even in identical twins. Each patient presents their own unique profile of symptoms and signs. Males and females are equally affected. Undiagnosed older children and adults are often only ascertained due to behavioral problems or school performance. In some cases, adults are only diagnosed when they have an affected child. Over 180 clinical features have been described in association with 22qDS, none of which in isolation is considered pathognomonic for the condition (Koczkowska et al, "Genomic findings in patients with clinical suspicion of 22q11.2 deletion syndrome" Journal Appl Genetics 2017 58:93-98).

The most common medical problems include congenital heart defects (primarily conotruncal abnormalities such as Tetralogy of Fallot), facial and palatal abnormalities, immunodeficiency, and hypocalcemia. There is a very wide range in the severity of these effects from life threatening to very minimal or symptomatic and undiagnosed. The neurocognitive profile is highly variable (both inter- and intra-individual). Typically, early in infancy motor delays (hypotonia) and speech and language delays are evident. The majority of patients fall into an IQ range of 70 to 84. These patients are also at an increased risk to develop ADHD, autism spectrum disorder (ASD), anxiety and mood disorders as well as psychotic disorders and schizophrenia. This complex behavioral/psychiatric phenotype changes across ages particularly with the risk of development of schizophrenia (Swillen, "Developmental Trajectories in 22q11.2 deletion" Am J Med Genet C Semin Med Genet June 2015).

In children, developmental delays are common, including mild intellectual delay and/or learning disability with an average IQ around 70.

The present disclosure relates to a method of treating one or more behavioral symptoms of 22q11.2 deletion syndrome in a subject by administering an effective amount of cannabidiol (CBD) to the subject wherein one or more behavioral symptoms of 22q11.2 deletion syndrome are treated in the subject. Administering the effective amount of CBD includes transdermally or orally administering.

The present disclosure also relates to a method of treating a human suffering from 22q11.2 deletion syndrome by administering a therapeutically effective amount of synthetic or purified cannabidiol to the human suffering from the 22q11.2 deletion syndrome to effectively treat the 22q11.2 deletion syndrome in the human in need thereof. The cannabidiol can be administered transdermally or orally.

CBD has a modulating effect on the endocannabinoid system, agonist effect on serotonin$_{1a}$ receptors, and antagonist effect of the G-protein coupled receptor GPR55. Transdermal or oral administration of an effective amount of CBD gel can be an effective treatment for the behavioral phenotypes of 22q11.2 deletion syndrome, for example, general anxiety.

Anxiety in individuals can disrupt development and quality of life of individuals suffering from 22q11.2 deletion syndrome more than IQ. Anxiety, not IQ, can predict the adaptive functioning of individuals with 22q11.2 deletion syndrome. Controlling anxiety in children, for example, in children six-years old to adolescent, the development of psychosis can be prevented or delayed. Addressing anxiety and mental health issues in patients with 22q11.2 deletion syndrome can improve quality of life of these individuals.

Other symptoms that can be treated include psychosis, mood disorders, emotional and behavioral issues, and/or attention-deficit/hyperactivity disorder (ADHD).

In some embodiments, transdermal delivery of cannabinoids (e.g., CBD) has benefits over oral dosing because it allows the drug to be absorbed through the skin directly into the bloodstream. This avoids first-pass liver metabolism, potentially enabling lower dosage levels of active pharmaceutical ingredients with a higher bioavailability and improved safety profile. Transdermal delivery also avoids the gastrointestinal tract, lessening the opportunity for GI related adverse events and the potential degradation of CBD by gastric acid into THC, which can be associated with unwanted psychoactive effects. Moreover, transdermal delivery of CBD reduces the intensity and frequency of somnolence adverse events, which are typically present in oral dosing of CBD. Transdermal delivery of CBD can avoid liver function adverse events, which are typically present in oral dosing of CBD. In some embodiments, transdermally administering an effective amount of CBD reduces an intensity of at least one adverse event by about 15% to about 95% relative to orally administering CBD.

The CBD can be in a gel form and can be pharmaceutically-produced as a clear, permeation-enhanced gel that is designed to provide controlled drug delivery transdermally or orally with once- or twice-daily dosing. The CBD gel can be between 1% (wt/wt) CBD to 7.5% (wt/wt) CBD. The CBD gel can have, for example, 4.2% (wt/wt) CBD or 7.5% (wt/wt) CBD). The CBD gel can be applied topically by the patient or caregiver to the patient's upper arm and shoulder, back, thigh, or any combination thereof. The CBD can be applied orally by the patient, the caregiver, or a combination thereof.

The CBD gel can include diluents and carriers as well as other conventional excipients, such as wetting agents, preservatives, and suspending and dispersing agents.

The CBD gel can include a solubilizing agent, a permeation enhancer, a solubilizer, antioxidant, bulking agent, thickening agent, and/or a pH modifier. The composition of the CBD gel can be, for example, a. cannabidiol present in an amount of about 0.1% to about 20% (wt/wt) of the composition; b. a lower alcohol having between 1 and 6 carbon atoms present in an amount of about 15% to about 95% (wt/wt) of the composition; c. a first penetration enhancer present in an amount of about 0.1% to about 20% (wt/wt) of the composition; and d. water in a quantity sufficient for the composition to total 100% (wt/wt). Other formulations of the CBD gel can be found in International Publication No. WO 2010/127033, the entire contents of which are incorporated herein by reference.

The effective amount of CBD can be between about 50 mg to about 1000 mg daily, which can be administered in a single daily dose or twice daily dosing.

Example 1: Common Behavioral Features of Autism, Fragile X Syndrome, and 22q11.2 Deletion Syndrome Autism Spectrum Disorder (ASD), Fragile X Syndrome (FXS), 22q11.2 deletion syndrome (22qDS) are complex neurodevelopmental conditions with considerable overlap in neuropsychological and behavioral symptomatology. ASD is characterized by problems in social communication and social interaction, as well as restricted and repetitive patterns of behavior, interests, or activities. FXS is a rare genetic condition caused by CGG repeat expansion in the FMR1 (fragile X mental retardation 1) gene located on the X chromosome; behavioral symptoms can include social withdrawal, anxiety, avoidance of eye contact, sensory hypersensitivity, echolalia, and hand flapping. 22qDS is one of the most common microdeletion syndromes and often involves behavioral symptoms of social limitations and difficulty in maintaining relationships with peers.

The socio-behavioral deficits seen in ASD and FXS have been attributed to dysregulation of the endocannabinoid systems, which is comprised of (1) two G-protein-coupled receptors (a) cannabinoid receptor type 1 ($CB_1$), located primarily in the CNS and (b) cannabinoid receptor type 2 ($CB_2$), located in multiple systems throughout the body; and (2) endogenous *cannabis*-like ligands (endocannabinoids) that bind to CB1 receptors and modulate synaptic transmission throughout the CNS; the two best described are anandamide (AEA) and 2-arachidonoylglycerol (2-AG).

Cannabidiol (CBD) is a non-euphoric cannabinoid. CBD has low affinity for $CB_1$ and $CB_2$ receptors, yet the vast chemogenomic targets suggest a broad polypharmacology for CBD producing a wide spectrum of physiological responses, including antagonism of GPR55 (a G-protein coupled receptor located in the caudate nucleus and putamen); partial agonism of $5-HT_{1A}$ receptors; promotion of intracellular calcium release and peroxisome proliferator-activated receptor-gamma agonism; and allosteric modulation of mu- and delta-opioid receptors.

Objective: The objective of this study was to conduct a retrospective literature review on patients with ASD, FXS, and 22qDS to determine the nature and extent of symptomatic overlap in these conditions and to suggest a possible role for CBD in the management of these shared symptoms based on insights from an open-label, 12-week study evaluating the safety, tolerability and initial efficacy of transdermal CBD for the treatment of behavioral and emotional symptoms associated with child/adolescent FXS. (Heussler et al., *A phase 1/2, open-label assessment of the safety, tolerability, and efficacy of transdermal cannabidiol (ZYN002) for the treatment of pediatric fragile X syndrome*; J. Neurodev Disorder. 2019; 11(1): 16)

Methods: A search of the PubMed database was conducted using the terms "behavior," "behavioral symptoms," "autism spectrum disorder," "ASD," "Fragile X Syndrome," "FXS," "22q11.2 deletion syndrome," "parents," "caregivers," and "CBD and treatment of anxiety" with no restriction on date or publication type. Records were analyzed for relevance.

Results

All Conditions: The most common behavioral manifestations across all conditions are anxiety-related; such as social avoidance, irritability, attention deficits, stereotypy, poor communication, and social unresponsiveness. See FIG. 1, Common Behavioral Features of ASD, FXS, and 22q11DS.

ASD: Anxiety-related symptoms are common in patients with ASD, with up to 84% of children experiencing some degree of debilitating anxiety; rates of physician-diagnosed anxiety disorders range from 42-55% and may include simple phobias, generalized anxiety disorder, separation anxiety disorder, obsessive-compulsive disorder, and social phobias. Comorbid anxiety disorders can be broad-ranging and associated with behaviors such as aggression/irritability and isolation from same-age peers. Inattention and hyperactivity are often present in Attention Deficit-Hyperactivity Disorder and ASD, and they are common to their respective diagnostic criteria. Children with ASD who have severe intellectual disability ([ID] IQ<40) showed higher levels of psychiatric symptoms (anxiety, mood, sleep, organic syndromes, and stereotypies/tics) than those with ID but no ASD.

FXS: In FXS, severe cognitive and social impairments are more common in males than in females. FXS usually has profound effects on the life of patients (comorbid conditions, social impairment) as well as their caregivers and families (mental health, absence from work/school). Anxiety and social avoidance are considered core features of FXS. Social avoidance has been defined as a behavioral response to anxiety that arises from fear of social interaction; thus, anxiety can be thought of as a foundational precipitant to social avoidance. Social avoidance encompasses behaviors that may include seeking isolation (e.g., stay in their room to avoid others), lack of interaction, social escape (e.g., face-hiding, leaning away), and gaze avoidance that distance the individual from his/her social counterparts. Variation in FMR1 protein expression has been linked to avoidance behaviors among females with the disorder. In a study that used interviews of parents/caregivers (n=97) of boys and girls with FXS to determine the prevalence of anxiety (based on DSM-IV criteria), 82.5% of participants had at least 1 anxiety disorder, irrespective of sex, age, presence of autism, or IQ, with the most common diagnoses being specific phobia (59.6%); social phobia (58.3%); selective mutism (25.3%); generalized anxiety disorder (23.7%); and obsessive-compulsive disorder (23.7%). The presence of ID in patients with FXS impairs their ability to self-report symptoms of worry and fear, increasing reliance on caregiver observations of outward behavioral manifestations of anxiety characteristics, which may include any of the following: social avoidance; nervous behavior during social situations; shyness; refusal of activities with social demands; poor understanding of social cues from inattention to faces, socioemotional processing, social skills during interpersonal interactions; fearfulness; social escape behaviors.

22QDS: The most common behavioral/psychiatric diagnoses in children with 22qDS are ADHD, ASD, and anxiety. A large-scale, collaborative study (>1400 participants aged 6-68 yrs) reported ADHD in 37% of 6-12 year-olds and in nearly 24% of 13-17 year-olds; ASD peaked in 13-17 year-olds (25.4%); anxiety disorders were more prevalent than mood disorders at all ages, but especially in children and adolescents with at least 33% of 6-17 year-olds reporting anxiety disorder. Up to one-third of patients with 22qDS will develop schizophrenia and schizo-affective disorder by late adolescent and early adulthood, and over 40% of patients have been reported to a schizophrenic spectrum disorder after 25 years of age. Although these diagnoses are reported in individuals with 22qDS, the diagnosis of ASD is particularly controversial in this population and may be related to poor clinical understanding of the typical behavioral phenotype. The emergence of social deficits during adolescence can represent a major source of disability in some individuals with 22qDS; cross-sectional studies show that children with 22qDS are withdrawn and shy and have social impairments which may be less of a concern to the individual.

Role of CBD: CBD has diverse pharmacologic effects. Based on findings from an open-label study in children/adolescents with FXS (Heussler et al., *A phase 1/2, open-label assessment of the safety, tolerability, and efficacy of transdermal cannabidiol (ZYN002) for the treatment of pediatric fragile X syndrome*; J. Neurodev Disorder. 2019; 11(1): 16) and a retrospective literature review, CBD may improve multiple symptoms experienced by patients with ASD, FXS, and 22qDS, and it is generally well tolerated in children and adults. Results from receptor pharmacology studies investigating the possible role of CBD in the treatment of behavioral symptoms associated with ASD, FSX, and 22qDS suggest (1) a role for the endocannabinoid system in regulating behavioral symptoms and (2) the pharmacology of CBD is broad, continues to be defined, and may prove beneficial in addressing important symptoms. Findings from the first crossover trial testing the effects of CBD on symptoms of social anxiety in adults with social phobia found significant and clinically meaningful reductions in both physiological and cognitive indicators of anxiety, which may translate to therapeutic effects in patients with ASD, FXS, and 22qDS. A recent case series provided initial evidence that CBD may lead to broad improvement in childhood FXS symptomology, including symptoms of anxiety and social avoidance. An open-label, 12-week study evaluated the safety, tolerability and initial efficacy of transdermal CBD for the treatment of behavioral and emotional symptoms associated with child/adolescent FXS and found both positive effects on the emotional and behavioral symptoms of FXS, including for many, an increase in social confidence which may be translatable to the other defined populations.

Conclusions: Patients with ASD, FXS, and 22qDS share a constellation of socio-behavioral symptoms that includes anxiety, leading to seeking isolation behavior (social avoidance), irritability, attention deficits, and poor communication. Preliminary evidence shows that CBD improves social anxiety and associated behavioral manifestations suggesting that CBD may prove to be effective in managing the spectrum of behavioral symptoms associated with these conditions.

Example 2: An Open-Label, Tolerability and Efficacy Study of ZYN002 Administered as a Transdermal Gel to Children and Adolescents with 22q11.2 Deletion Syndrome Objectives: The primary objective is to evaluate the safety and tolerability of ZYN002 administered as a transdermal gel formulation, for up to 38 weeks, in patients ages 6 to <18 years, in the treatment of 22q11.2 Deletion Syndrome (22qDS). The secondary objectives include (1) to evaluate the efficacy of ZYN002 in the treatment of symptoms of 22q11DS and (2) to evaluate cannabidiol (CBD) and tetrahydrocannabinol (THC) plasma level exposure. The identification of plasma levels of CBD metabolites may be conducted as an exploratory objective.

Methodology: This is an open-label study to assess the safety, tolerability and efficacy of CBD administered as ZYN002, a transdermal gel, for the treatment of child and adolescent patients with 22qDS. Male and female patients with 22qDS will be treated in Period 1 for 14 weeks with 250 mg and 500 mg of CBD (patients ≤35 k Kg will receive 250 mg CBD daily; patients >35 Kg will receive 500 mg CBD daily). For patients with less than a 25% improvement from baseline in the ABC-C irritability subscale, the investigator may increase the total daily dose at Week 6 of treatment. Approximately 20 male and female patients, ages 6 to <18 years, will receive ZYN002.

During screening procedures, the following scales will be administered:
Aberrant Behavior Checklist (ABC-C)
Autism Diagnostic Observation Schedule®-2 (ADOS®-2) (Note: is not administered at Screening if it has been administered in the prior 6 months and the results are available)
Clinical Global Impression-Severity (CGI-S)
Columbia-Suicide Severity Rating Scale—Children's version (C-SSRS)
Anxiety, Depression and Mood Scale (ADAMS)
Qualitative Caregiver Reported Behavioral Problems Survey
Children's Sleep Habits Questionnaire (CSHQ)
Pediatric Anxiety Rating Scale-Revised (PARS-R)

14-Week and 24-Week Extension Open Label Treatment Period: Following the Screening Period, eligible patients will receive ZYN002 on Study Day 1 (Visit 2). There must be at least 7 days between Visit 1 (Screening) and Visit 2 (Day 1).

Patients and parents/caregivers will be required to visit the clinic at Day 1/Visit 2, Week 6/Visit 3, and Week 14/Visit 4, for the collection of: vital signs, ECG, concomitant medication review, physical and neurological exam, pregnancy tests, skin assessment exam (Day 1) and skin irritation examination (Visits 3 and 4), adverse event (AE) review, and questionnaire and scale completion.

Patients that complete Visit 4 and have a ≥35% improvement on the ABC-C irritability subscale will be allowed to continue to Period 2 for an additional 24 weeks of treatment. Period 2 will have additional Visits at Week 22/Visit 5, Week 30/Visit 6, and Week 38/Visit 7.

The following questionnaires and scales will be administered at Visit 2, Visit 3, Visit 4, Visit 5 and Visit 7, unless an exception is noted:
  ABC-C
  CGI-S
  Clinical Global Impression-Improvement (CGI-I) (not completed on Visit 2, Day 1)
  ADAMS
  C-SSRS
  Qualitative Caregiver Reported Behavioral Problems Survey (not completed at Visit 2)
  Children's Sleep Habit Questionnaire
  PARS-R Safety Monitoring: Patient safety will be monitored at each study visit using standard measures, including physical and neurological exams, examination of skin at application sites for irritation, vital signs (including oral, infrared forehead or tympanic temperature), 12-lead ECGs, the C-SSRS, safety laboratory tests, and AE monitoring.

Number of Patients (Planned): Approximately 20 male and female patients will be enrolled. Patients who prematurely discontinue after Visit 2 will not be replaced.

Select Inclusion Criteria: Male or female children and adolescents aged 6 to <18 years, at the time of Screening. Patients must have a diagnosis of 22qDS confirmed by genetic testing, with or without autistic features. Patients have a CGI-S score of 4 or higher at Screening Visit 2. Patients must have a score of the ABC-C Irritability Subscale of 18 or higher at Screening and Visit 2. Patients with a history of seizure disorders must currently be receiving treatment with a stable regimen of one or two AEDs, or must be seizure-free for one year if not currently receiving AEDs.

Treatment Period: This study has a 14-Week Treatment Period and a 24-Week Extension Period, as follows:
  Patients weighing ≤35 kg will receive 125 mg CBD applied Q12H (±2 hours); total daily dose of 250 mg CBD. Each application will consist of one sachet of ZYN002 CBD 4.2% concentration, containing 2.98 g of gel. At Week 6, if the patient has less than a 25% improvement from baseline in the ABC-C irritability subscale, the investigator may increase the dose as follows:
    Patients who weigh ≤35 kg receiving a total daily dose of 250 mg CBD may increase to a daily dose of 500 mg. Each application will consist of two sachets of ZYN002 CBD 4.2% concentration, containing 2.98 g of gel.
  Patients >35 kg will receive 250 mg CBD applied Q12H (±2 hours); total daily dose of 500 mg CBD. Each application will consist of two sachets of ZYN002 CBD 4.2% concentration, each sachet containing 2.98 g of gel. At Week 6, if the patient has less than a 25% improvement from baseline in the ABC-C irritability subscale, the investigator may increase the dose as follows:
    Patients who weigh >35 kg receiving a daily dose of 500 mg CBD may increase the daily dose to 750 mg. Each application will consist of three sachets of ZYN002 CBD 4.2% concentration, containing 2.98 of gel.

Duration of Treatment: Parents/caregivers will apply study drug twice daily for up to 24 weeks.

Statistical Methods: Descriptive statistics (mean, median, standard deviation, minimum, and maximum) for continuous data and number (n) and percentage (%) for categorical data will be presented for all efficacy and safety parameters.

All efficacy assessments will be summarized at Visits 3, 4, 5, 6 and 7.

Safety assessments (actual and change from screening) taken at study Day 1, Visits 3, 4, 5, 6 and 7 will be summarized using descriptive statistics and presented by maintenance dose.

What is claimed is:

1. A method of treating one or more behavioral and/or psychiatric symptoms of 22q11.2 deletion syndrome in a subject, the method comprising:
   administering an effective amount of cannabidiol (CBD) to the subject wherein one or more behavioral and/or psychiatric symptoms of 22q11.2 deletion syndrome are treated in the subject.

2. The method of claim 1, wherein the administration of CBD is effective for the treatment of general anxiety in the subject.

3. The method of claim 1, wherein the CBD is (−)-CBD.

4. The method of claim 1, wherein the effective amount of CBD is between about 50 mg and about 1000 mg total daily.

5. The method of claim 1, wherein the CBD is formulated as a gel.

6. The method of claim 1, wherein the CBD is administered in a single daily dose.

7. The method of claim 1, wherein the CBD is administered in two daily doses.

8. The method of claim 1, wherein the CBD is formulated as a permeation-enhanced gel.

9. The method of claim 1, wherein the CBD is transdermally administered on the subject's arm.

10. The method of claim 1, wherein the CBD is a synthetic CBD.

11. The method of claim 1, wherein the CBD is botanically derived.

12. The method of claim 1, wherein the CBD is purified.

13. The method of claim 1, wherein administering comprises transdermally administering.

14. The method of claim 13, wherein transdermally administering an effective amount of cannabidiol (CBD) reduces an intensity of at least one adverse event relative to orally administering CBD.

15. The method of claim 14, wherein the at least one adverse event is selected from the group consisting of somnolence, psychoactive effects, liver function, and GI related adverse events.

16. The method of claim 1, wherein the effective amount of CBD is about 125 mg total daily.

17. The method of claim 1, wherein the effective amount of CBD is about 250 mg total daily.

18. The method of claim 1, wherein the effective amount of CBD is about 500 mg total daily.

19. The method of claim 1, wherein the effective amount of CBD is about 750 mg total daily.

20. The method of claim 1, wherein the effective amount of CBD is about 1000 mg total daily.

* * * * *